(12) United States Patent
Bowers

(10) Patent No.: US 7,822,471 B2
(45) Date of Patent: Oct. 26, 2010

(54) METHOD AND APPARATUS FOR DETECTING ARTIFACT SIGNALS IN THE ELECTROCARDIOGRAM OF A PATIENT CAUSED BY CPR AND/OR PATIENT MOTION USING PATIENT IMPEDANCE

(75) Inventor: Kyle R. Bowers, Boxborough, MA (US)

(73) Assignee: Access CardioSystems, Inc., Concord, MA (US)

(*) Notice: Subject to any disclaimer, the term of this patent is extended or adjusted under 35 U.S.C. 154(b) by 0 days.

(21) Appl. No.: 11/192,781

(22) Filed: Jul. 29, 2005

(65) Prior Publication Data
US 2006/0025825 A1 Feb. 2, 2006

Related U.S. Application Data

(60) Provisional application No. 60/592,993, filed on Jul. 30, 2004.

(51) Int. Cl.
*A61B 5/04* (2006.01)
(52) U.S. Cl. .................. 600/513; 600/527; 600/534
(58) Field of Classification Search .......... 600/513, 600/527, 534
See application file for complete search history.

(56) References Cited

U.S. PATENT DOCUMENTS

| | | | | |
|---|---|---|---|---|
| 5,247,939 A | * | 9/1993 | Sjoquist et al. | 600/510 |
| 5,704,365 A | * | 1/1998 | Albrecht et al. | 600/515 |
| 5,957,856 A | * | 9/1999 | Weil et al. | 600/518 |
| 6,125,299 A | | 9/2000 | Groenke et al. | |
| 6,287,328 B1 | | 9/2001 | Snyder et al. | |

(Continued)

OTHER PUBLICATIONS

Fitzgibbon et al., Determination of the Noise Source in the Electrocardiogram During Cardiopulmonary Resuscitation, Critical Care Medicine, 2002, vol. 30, No. 4.

(Continued)

*Primary Examiner*—Carl H Layno
*Assistant Examiner*—Natasha N Patel
(74) *Attorney, Agent, or Firm*—Pandiscio & Pandiscio

(57) ABSTRACT

Medical apparatus for detecting the presence of artifact signals generated in the electrocardiogram of a patient by CPR and/or other patient motion. The presence of artifact signals is determined by analyzing variations in a measured electrical signal that represents the patient's transthoracic impedance. Such detection is important because the presence of CPR and/or motion artifacts can disrupt a patient's electrocardiogram (ECG) signal. The patient's impedance signal data is stored in the apparatus and analyzed to determine if the characteristics are indicative of the presence of CPR and/or motion artifacts. This analysis is performed independently of ECG data and may be used as an indicator of the underlying ECG rhythm classification. In essence, if the impedance exceeds some threshold amount, so as to indicate the presence of CPR or patient motion which can render the ECG data unreliable, the normal interpretation of the ECG data is interrupted. Applications of the invention include, but are not limited to, advising or not advising, defibrillation therapy, CPR or intravenous medicinal therapy.

8 Claims, 12 Drawing Sheets

U.S. PATENT DOCUMENTS

| | | | |
|---|---|---|---|
| 6,304,773 B1 | 10/2001 | Taylor et al. | |
| 6,351,671 B1 | 2/2002 | Myklebust et al. | |
| 6,847,737 B1* | 1/2005 | Kouri et al. | 382/260 |
| 6,961,612 B2* | 11/2005 | Elghazzawi et al. | 607/6 |
| 2003/0060723 A1* | 3/2003 | Joo et al. | 600/510 |

OTHER PUBLICATIONS

Husoy et al., Removal of Cardiopulmonary Resuscitation Artifacts From Human ECG Using an Efficient Matching Pursuit-Like Algorithm, IEEE Transactions on Biomedical Engineering, Nov. 2002, vol. 49, No. 11.

Van Alem et al., Interruption Of Cardiopulmonary Resuscitation With the Use of the Automated External Defibrillator in Out-Of-Hospital Cardiac Arrest, Annals of Emergency Medicine, Jul. 2003.

Yu et al., Adverse Outcomes of Interrupted Precordial Compression During Automated Defibrillation, American Heart Association Circulation, Jul. 16, 2002.

* cited by examiner

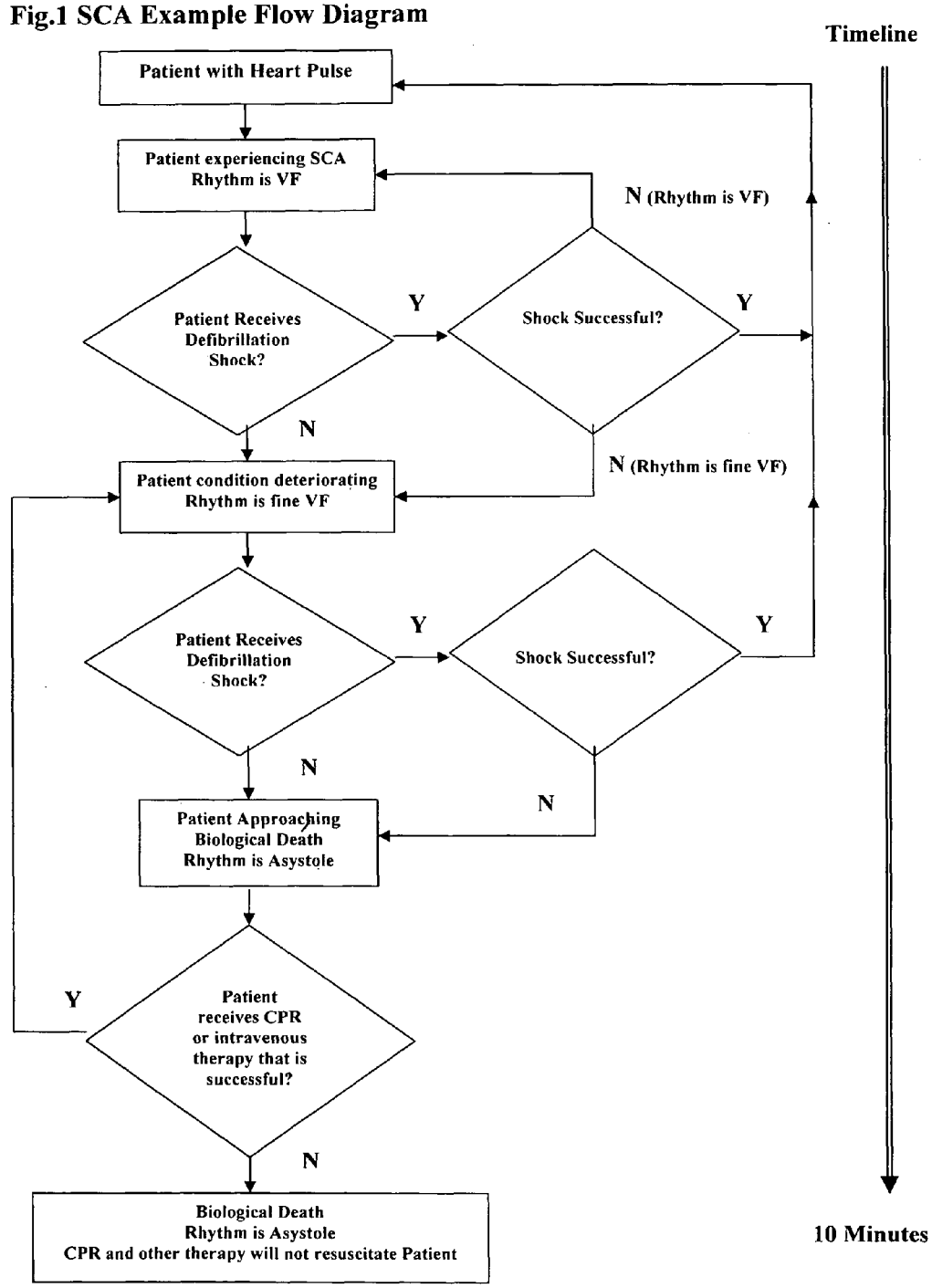

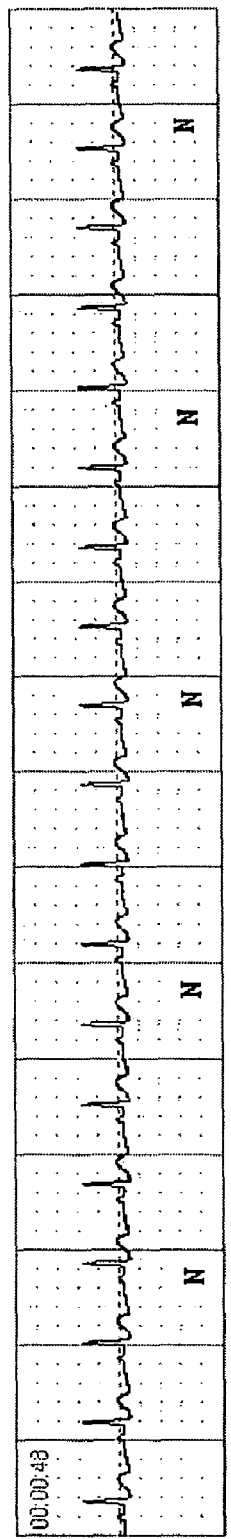
Fig. 2 Normal Sinus Rhythm

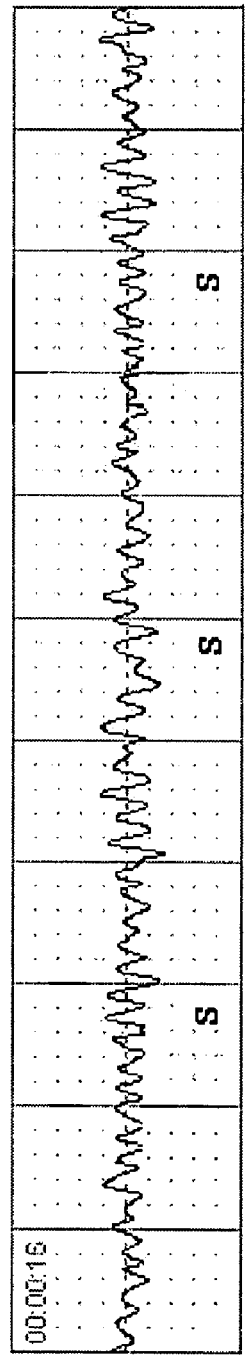
Fig 3 Ventricular Fibrillation (VF)

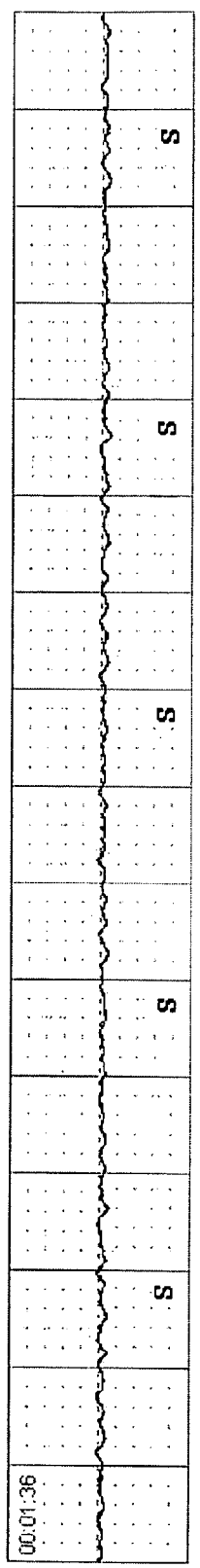
Fig. 4 Fine VF

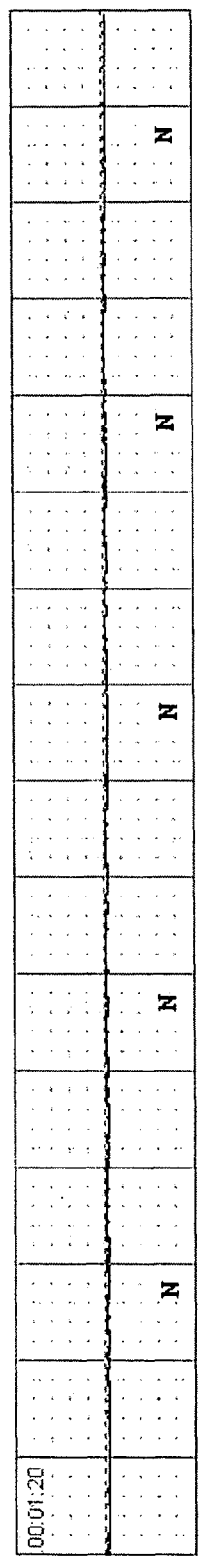
Fig. 5 Asystole

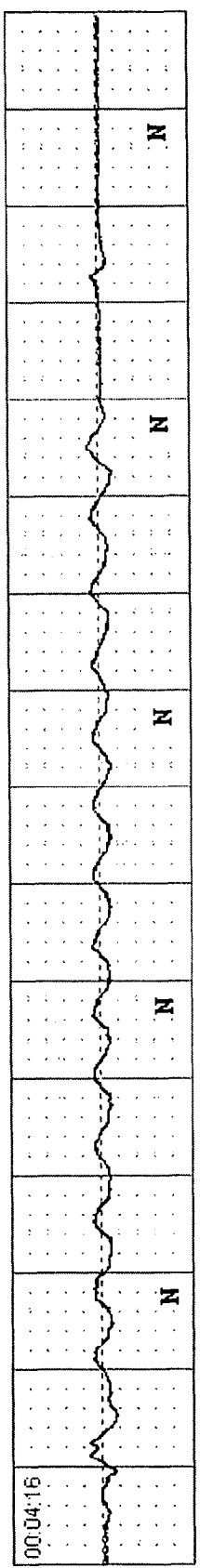
Fig. 6A CPR over Asystole
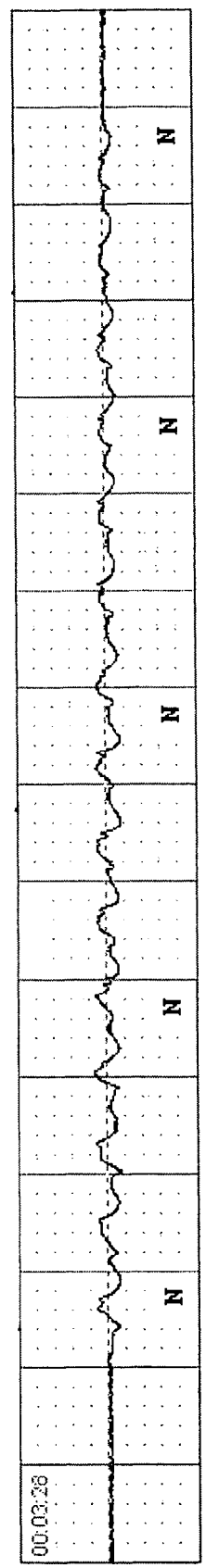
Fig. 6B CPR over Asystole

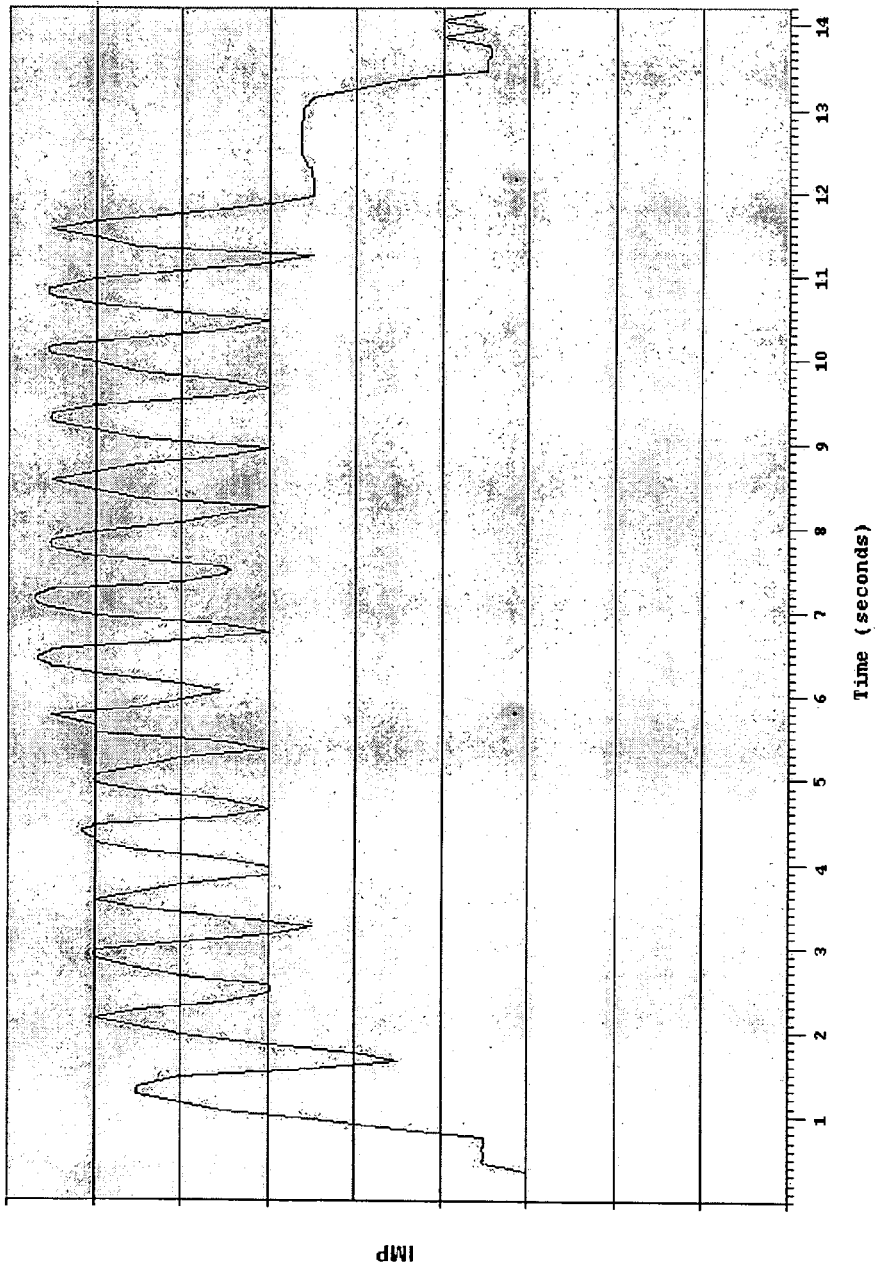

Fig. 9 System Block Diagram

Fig. 10 Impedance Sensing Block Diagram

Fig. 12 Example Impedance Threshold Values For Each AED Mode Of Operation
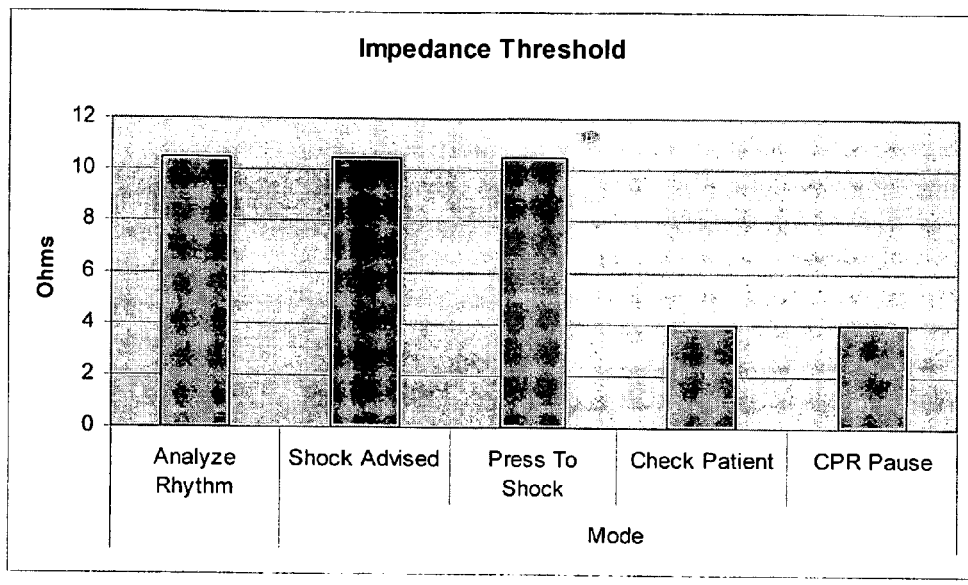

METHOD AND APPARATUS FOR DETECTING ARTIFACT SIGNALS IN THE ELECTROCARDIOGRAM OF A PATIENT CAUSED BY CPR AND/OR PATIENT MOTION USING PATIENT IMPEDANCE

REFERENCE TO PENDING PRIOR PATENT APPLICATION

This patent application claims benefit of pending prior U.S. Provisional Patent Application Ser. No. 60/592,993, filed Jul. 30, 2004 by Kyle R. Bowers for METHOD AND APPARATUS FOR CPR AND ARTIFACT DETECTION USING PATIENT IMPEDANCE, which patent application is hereby incorporated herein by reference.

FIELD OF THE INVENTION

This invention relates to the measurement and analysis of impedance signal variations in a patient. More particularly, the present invention relates to a method and apparatus for detecting artifact signals in the electrocardiogram of a patient caused by CPR and/or patient motion.

BACKGROUND OF THE INVENTION

An electrocardiogram (ECG) represents the electrical activity of a patient's heart (see FIG. 2). In general, cardiac monitoring and resuscitation devices use the ECG waveform to determine the condition of a patient's heart. Using sophisticated algorithms, these devices analyze the heart's rhythm to determine if the patient requires therapy. More particularly, automatic external defibrillators (AEDs) use these algorithms to determine if a patient's rhythm is shockable, such as in the case of ventricular fibrillation (see FIG. 3) or high-rate ventricular tachycardia. AEDs also use these algorithms to determine if a patient's rhythm is non-shockable, such as where the ECG waveform contains QRS complexes (i.e., where a series of deflections in an electrocardiogram represents electrical activity generated by ventricular depolarization prior to contraction of the ventricles) or where the patient is experiencing fine VF (below the shockable threshold) (see FIG. 4) or asystole (see FIG. 5).

One common problem with analyzing a patient's rhythm is the introduction of an artifact signal into the ECG. It is difficult for cardiac devices and monitoring devices to distinguish common artifact signals from the underlying rhythm in the ECG signal.

An artifact signal can be introduced by CPR or by motion of the patient during respiration or transport. Such CPR artifact signals originate at the patient's electrode-skin interface when the rescuer compresses the patient's chest. If the device analyzing the patient's rhythms has large electrode pads, such as an AED, the rescuer may touch the pad when performing chest compressions, thereby further aggravating the problem of misleading artifacts.

One specific area of concern is with low cost AEDs and monitoring devices. These devices must analyze the patient's rhythm without some explicit indication of the events causing the artifact signals described above. In addition, these low cost devices may lack the sophisticated electronics, sensors and/or other resources which may be used to detect these artifact signals.

In some instances, e.g., where CPR is performed correctly, the artifact signal is generally sinusoidal in appearance (FIG. 6A). However, if CPR is performed by a layperson or performed during transport, the artifact signal superimposed over a patient's underlying non-shockable ECG rhythm may appear shockable to the analyzing device. In some specific cases, the resulting rhythm may begin to look like ventricular fibrillation (FIG. 6B). The analyzing device may misinterpret the rhythm as shockable and prompt the rescuer to "Stand Clear" and stop performing CPR. Then, the device analyzes the ECG without the artifact signal, determines that the rhythm is non-shockable, and the result is that the rescuer is delayed in performing the necessary CPR therapy. As is well known in the art, delays in performing CPR on a cardiac arrest victim may compromise the outcome of a successful resuscitation.

In cases where significant patient motion creates an artifact signal, the super-imposed ECG rhythm may also appear shockable. As is well known to those skilled in the art, certain motion environments, such as those of fixed-wing aircraft or helicopters, can introduce a vibration at a resonant or harmonic frequency which is related to the fundamental frequency of the source (i.e., the aircraft engine), and this can sometimes cause the monitoring equipment to falsely report a shockable event.

Thus, there is a need for a new and low cost approach for detecting the artifact signals introduced by CPR and/or patient motion, whereby to improve determinations of shockable conditions by monitoring devices.

SUMMARY OF THE INVENTION

It has now been recognized that the transthoracic impedance of the patient varies during CPR (see FIG. 7) and significant patient motion, and this phenomena can be used to identify the presence of CPR and/or motion artifacts in an ECG signal. More specifically, by measuring variations in a transthoracic impedance signal, it is possible to tell when a patient is undergoing CPR and/or in heavy motion, and thus when there may be CPR and/or heavy motion artifacts in an ECG signal.

Since the transthoracic impedance signal and the ECG signal do not correlate during CPR or heavy motion, these signals must be considered independently.

While the CPR-induced, and/or motion-induced, changes in the transthoracic impedance signal and the ECG signal generally time-correlate to one another, they do not share a simple transformation function, so it is generally simplest to consider the transthoracic impedance signal and the ECG signal separately from one another.

Therefore, the present invention provides a method and apparatus for detecting CPR and/or motion artifacts in the ECG signal of a patient by analyzing variations in a measured electrical signal that reflect changes in the patient's transthoracic impedance. By monitoring the impedance variations independently from ECG signal, this information may be used as an indicator of the underlying ECG rhythm classification, i.e. shockable or non-shockable rhythm, or to interrupt the ECG analysis altogether.

In accordance with one preferred embodiment of the present invention, the apparatus contains a microprocessor and circuitry configured to measure the patient's impedance, digitize the signal and store the digitized data in memory for analysis. The apparatus may also apply filtering techniques before and/or after storing the impedance signal data.

The characterization of the patient's impedance is generally achieved from an analysis of: (i) the baseline of the impedance signal data, (ii) amplitude variance of the impedance signal data, (iii) timing of the impedance signal data, and/or (iv) pattern recognition of the impedance signal data. In one embodiment of the present invention, a predetermined threshold may be applied to the amplitude variance. The present invention may also conditionally (or non-conditionally) use a combination or subset of the above-identified parameters. The above-identified parameters may also be weighted differently with respect to one another. Still other characterization techniques of the sort known in the art may be used for the analysis of the patient's impedance.

In analyzing the baseline of the impedance signal data, non-variance periods, signal averaging, or other techniques known in the art, may be used for the analysis of the patient's impedance.

In analyzing the amplitude or timing of the impedance signal data, trough-to-peak, peak-to-trough, baseline-to-peak, baseline-to-trough, peak-to-peak, trough-to-trough, rising slope, falling slope, Fast Fourier Transforms, or other techniques known in the art, may be used to detect the presence of CPR and/or motion artifacts in the ECG signal.

In one preferred embodiment of the present invention, predetermined thresholds are applied to the amplitude of the impedance signal data to detect the presence of CPR and/or motion artifacts in the ECG signal. These thresholds may be applied in different operating modes of the apparatus, e.g., "analyze rhythm", "shock advised", "press to shock", "check patient", "CPR pause", etc. A sophisticated analysis may be used to determine when the impedance variations have exceeded such predetermined thresholds.

The present invention may be implemented in a defibrillator that is configured to monitor the ECG signal for the presence of the CPR and/or motion artifacts in the ECG signal and, upon the detection of such CPR and/or motion artifacts in the ECG signal, interrupts the analysis of the patient's ECG rhythm.

In still another embodiment of the present invention, the characterization of the patient's impedance signal data is used by the apparatus to advise defibrillation therapy.

In yet another embodiment of the present invention, the characterization of the patient's impedance signal data is used by the apparatus to identify a non-shockable rhythm and to indicate to the user that defibrillation therapy is not advised.

In another embodiment of the present invention, the characterization of the patient's impedance signal data may be used by the apparatus to indicate a shockable ECG rhythm, in which case defibrillation therapy is advised, and CPR is not advised. In this situation, bystanders are advised to not touch the patient and stay clear of the patient.

And in another embodiment of the present invention, the characterization of the patient's impedance signal data is used by the apparatus to advise the user to apply CPR or intravenous medicinal therapy.

In one form of the invention, there is provided a method for detecting artifact signals in the electrocardiogram of a patient caused by CPR and/or patient motion, the method comprising:

acquiring impedance signal data from the patient; and analyzing variations in the acquired impedance signal data for characteristics indicative of artifact signals caused by CPR and/or patient motion.

In another form of the invention, there is provided an apparatus for detecting artifact signals in an electrocardiogram of a patient caused by CPR and/or patient motion, the apparatus comprising:

a signal circuit for passing an impedance-sensing signal through a patient;

an impedance measuring circuit connected to the signal circuit for measuring the impedance-sensing signal;

a conversion circuit for digitizing the impedance-sensing signal; and a microprocessor for analyzing the digitized signal data for characteristics indicative of CPR and/or patient motion.

In another form of the invention, there is provided a method for determining if a patient is undergoing CPR and/or motion, the method comprising:

passing an impedance-sensing signal through the chest of the patient; and analyzing variations in the impedance-sensing signal to determine when the patient is undergoing CPR and/or motion.

In another form of the invention, there is provided a method for treating a patient, the method comprising:

measuring the electrocardiogram of the patient and measuring variations in the transthoracic impedance of the patient;

determining when the patient is undergoing CPR and/or motion from variations in the transthoracic impedance;

applying conventional defibrillation therapy to the patient only if variations in the transthoracic impedance indicate that the patient is not undergoing CPR and/or motion.

In another form of the invention, there is provided a method for treating a patient, the method comprising:

measuring the electrocardiogram of the patient and measuring variations in the transthoracic impedance of the patient;

determining when the patient is receiving CPR from a rescuer, by analyzing variations in the transthoracic impedance;

allowing the rescuer to perform CPR therapy for a predetermined period of time;

stopping the rescuer from performing CPR after the predetermined period of time;

applying conventional defibrillation therapy to the patient only if variations in the transthoracic impedance indicate that the patient is not undergoing CPR and/or motion.

BRIEF DESCRIPTION OF THE DRAWINGS

These and other objects and features of the present invention will be more fully disclosed by the following detailed description of the preferred embodiments of the invention, which is to be considered together with the accompanying drawings wherein like numbers refer to like parts and further wherein:

FIG. 1 is a flow diagram of an example of a therapy decision chart for a Sudden Cardiac Arrest (SCA) over a timeline of 10 minutes—the corresponding patient rhythms are shown in FIGS. 2, 3, 4 and 5;

FIG. 2 is an exemplary ECG strip for a patient with a normal sinus rhythm—the non-shockable rhythm classification (N) is shown for each segment;

FIG. 3 is an exemplary ECG strip for a patient experiencing a Ventricular Fibrillation (VF) rhythm—the shockable rhythm classification (S) is shown for each segment;

FIG. 4 is an exemplary ECG strip for a patient experiencing a fine Ventricular Fibrillation rhythm—the shockable rhythm classification (S) is shown for each segment;

FIG. 5 is an exemplary ECG strip for a patient in asystole—the non-shockable rhythm classification (N) is shown for each segment;

FIGS. 6A and 6B are exemplary ECG strips where a patient is in asystole and a rescuer is performing CPR—the CPR rhythm is superimposed over the asystole rhythm;

FIG. 7 illustrates the transthoracic impedance signal corresponding to the ECG strip in FIG. 6A;

FIG. 12 is a diagram showing exemplary impedance threshold values for each AED mode of operation.

DETAILED DESCRIPTION OF THE PREFERRED EMBODIMENTS

Figure 8:
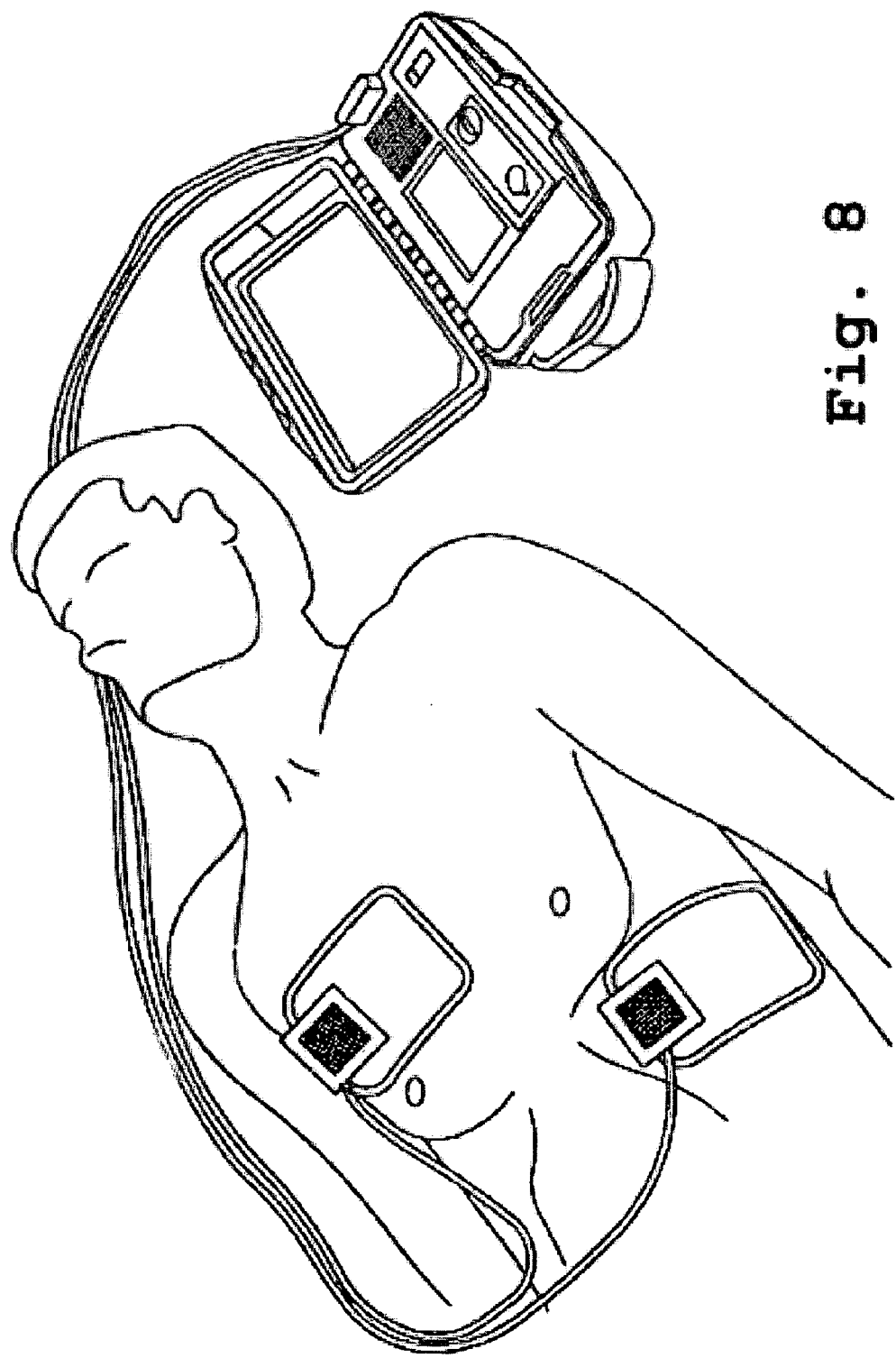
FIG. 8 illustrates a defibrillator and electrodes attached to the patient.

A device constructed in accordance with the present invention is configured to determine the presence of CPR or/motion artifacts in the patient's ECG by analyzing variations in a patient's transthoracic impedance. It should be appreciated that this device may be a patient monitoring device or a therapeutic device. By way of example, the device may be an AED, such as the one shown in FIG. 8. The patient is connected to the device via a pair of electrodes attached directly to the skin of the patient's chest.

A defibrillator uses the electrodes to provide a defibrillation shock to the heart of the patient, where the defibrillation shock is a pulsed electrical current, which passes through the patient's chest. In addition, the defibrillator uses the electrodes to sense ECG signals from the patient so as to determine the condition of the patient's heart and hence identify a shockable or non-shockable condition.

In accordance with the present invention, the electrodes may be further used in conjunction with impedance sensing circuitry in the defibrillator to detect changes in the patient's transthoracic impedance and hence determine if CPR and/or motion artifacts are present in the patient's ECG signal, such that the ECG signal may be unreliable for determining a shockable or non-shockable condition.

Figure 10:
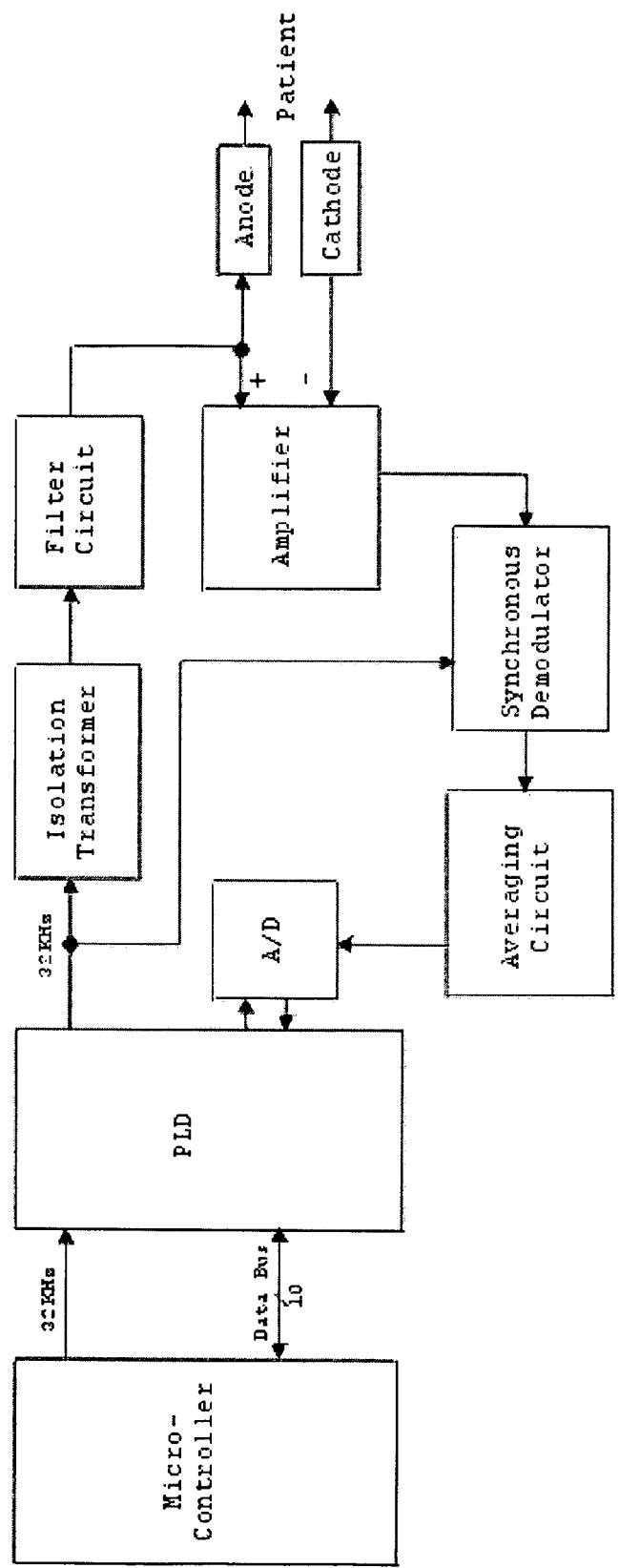
FIG. 10 is a block diagram of an impedance sensing circuit formed in accordance with the present invention.

Several techniques may be used for measuring patient transthoracic impedance. A block diagram of a form of impedance sensing circuit is shown in FIG. 10.

More particularly, the transthoracic impedance of a human body can be modeled as a resistor in series with a capacitor. The impedance circuit preferably uses a 32 KHz square wave voltage source, which is delivered to the patient via an isolation transformer and a filter circuit, which converts the input signal into a constant current sine wave. The constant current input signal applied to the patient produces an output signal having an output voltage in proportion to the patient's impedance. The impedance circuit synchronously demodulates and then averages the first 180 degrees of the output signal, which removes the capacitive reactance from the patient's impedance. The resulting DC voltage is directly proportional to the resistance of the patient's body.

Figure 9:
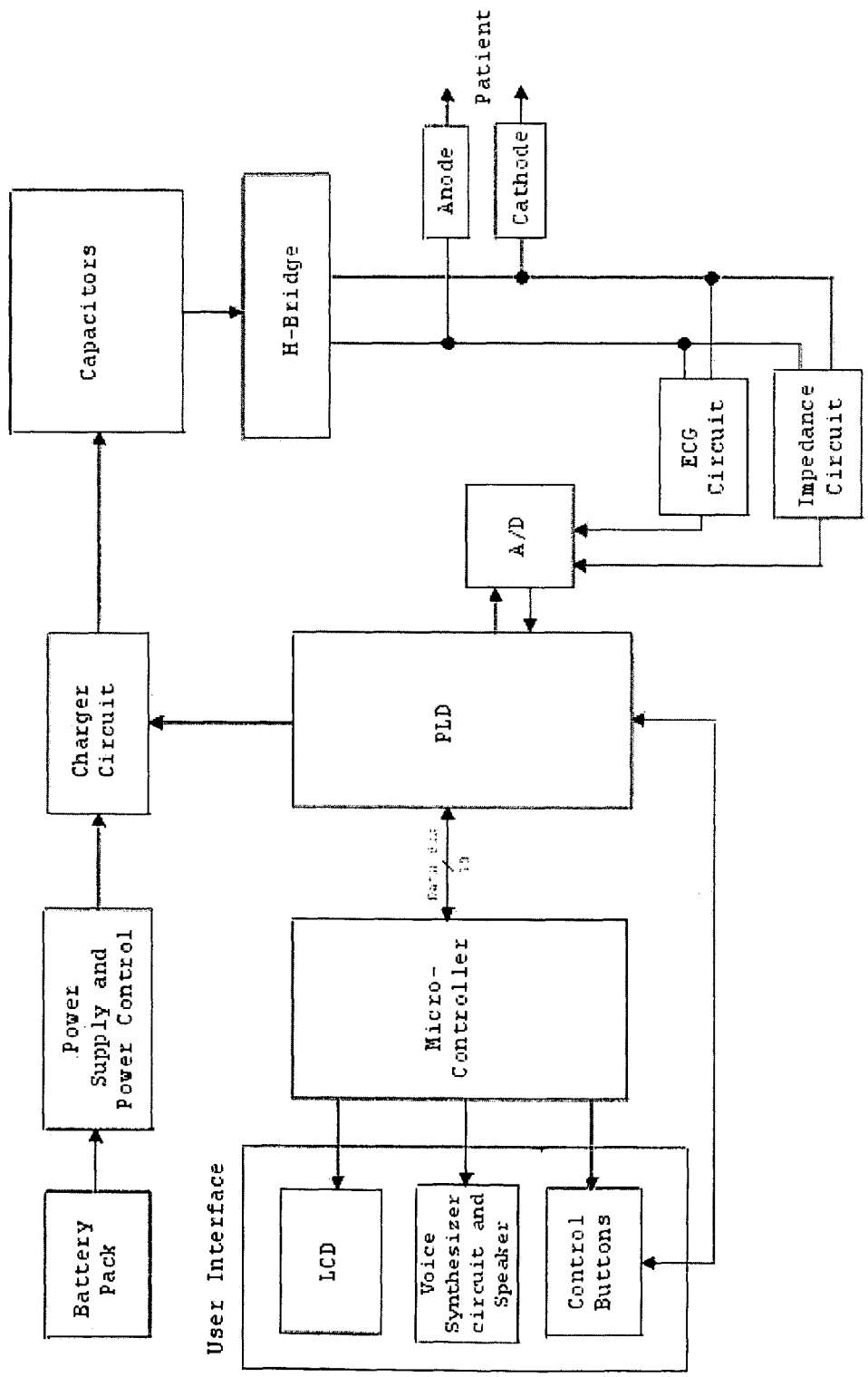
FIG. 9 is a block diagram of a defibrillator formed in accordance with the present invention.

A block diagram of the defibrillator components is shown in FIG. 9. The defibrillator contains a data acquisition system including, but not limited to, a microprocessor (microcontroller), programmable logic device (PLD), memory and an analog to digital converter (A/D). One preferred embodiment of the invention uses the microprocessor to periodically sample the impedance data of the output signal, store the data onto memory and process the data to determine variances in the impedance which indicate the presence of CPR and/or motion artifacts in the ECG signal. In one preferred embodiment of the present invention, the programmable logic device controls the interface to the analog to digital converter (A/D) and stores the sampled data into a local memory buffer. The programmable logic device then interrupts the microprocessor to sample the impedance data contained in the buffer via a data bus. The microprocessor may also be directly interfaced to the analog to digital converter and use internal timing or interrupts for the sampling frequency. Additionally, the microprocessor may be a microcontroller and have the memory, analog to digital converter and other peripherals on a single chip.

As is well known in the art, defibrillators generally comprise the circuitry for generating the defibrillation pulse including, but not limited to, a battery pack, a charger circuit, capacitors and an H-bridge circuit. The defibrillator of the present invention may also contain an LCD screen, voice synthesizer and speaker for instructing the rescuer.

The defibrillator data acquisition system of the present invention samples the thoracic impedance data on a regular interval, preferably every five milliseconds. The data acquisition system is preferably capable of measuring patient impedances from 10 ohms to 300 ohms, but could also measure other impedance ranges. The device stores the data in random access memory (RAM) for immediate processing, but may additionally store the data onto a removable flash card for post-incident analysis. The defibrillator may also store the data on other types of memory, including internal or external flash memory, magnetic media, optical media, etc.

Additionally, the defibrillator may apply digital filtering techniques before and/or after storing the impedance signal data.

As discussed above, the defibrillator also contains an ECG sensing circuit to determine the condition of the patient's heart. As is well known in the art, there are several techniques for sensing patient ECGs.

The ECG is typically sampled by the defibrillator data acquisition system in a similar manner to the technique described hereinabove. The defibrillator evaluates the patient's rhythm by looking for a regularly recurring QRS complex found in a normal ECG sinus rhythm, such as that shown in FIG. 2. When the device is not able to detect a normal ECG sinus rhythm, but instead finds an irregular rhythm, such as that illustrated in FIG. 3, or a shockable arrhythmia, such as a high rate ventricular tachycardia, the device follows a rescue protocol to provide therapy to the patient.

The defibrillator uses three-seconds of ECG data to create one data segment. The ECG data segment is classified in a binary fashion as either shockable or non-shockable. The ECG data segments are used to create a binary sequence of shockable or non-shockable segments. The sequence is then evaluated for the criterion of a shockable rhythm. This criterion may be "n-out-of-n" segments or related to a number of consecutive segments. The defibrillator begins to charge the capacitors and prepares to deliver therapy as long as the above criterion continues to be met.

An example scenario of sudden cardiac arrest (SCA) is shown in FIG. 1. In this example, the patient initially has a heart pulse. The initial rhythm may be normal, weak or an arrythmia. The patient experiences SCA when the heart rhythm transitions to VF due to one of many medical reasons. If the patient receives a shock within the first few minutes of the onset of VF, there is a strong likelihood that the VF rhythm will be eliminated and the patient's normal heartbeat restored. If the patient does not receive a defibrillation shock or the shock is unsuccessful, the rhythm eventually deteriorates toward fine VF over time.

There is a lower probability of resuscitating the patient when the rhythm reaches fine VF. The defibrillator of the present invention, however, uses a threshold to determine if the fine VF rhythm is still shockable. If the rhythm amplitude is below the threshold, the defibrillator will not declare a shockable rhythm. When the rhythm is below the shockable threshold, CPR and/or intravenous therapy is more effective for the patient. This therapy may once again stimulate the heart, so that defibrillation therapy can be applied.

A heart with no electrical activity is in asystole, as shown in FIG. 5. Without the flow of oxygen to the brain and other vital organs, the patient eventually reaches biological death.

When the patient is in fine VF below the threshold, or in asystole, the defibrillator of the present invention prompts the rescuer to begin administering CPR to the patient. During CPR, the patient's ECG may appear sinusoidal or semi-sinusoidal in nature.

However, in many cases, the rescuer may be poorly trained in CPR or in the process of transporting the patient into an ambulance. In this case, the ECG may not appear sinusoidal or semi-sinusoidal. More particularly, the ECG signal (which consists of the CPR signal superimposed over the fine VF or asystole ECG) may appear to resemble VF, as is shown in FIG. 3. In other words, where the patient is in fine VF below threshold or asystole, which would indicate a non-shockable condition, the application of non-ideal CPR or the occurrence of patient motion may alter the patient's ECG so that it appears similar to a VF condition, which is a shockable condition. Thus, the administration of non-ideal CPR or the occurrence of patient motion may modify the ECG signal so that a non-shockable condition appears as a shockable condition, thereby interfering with proper therapy. For this reason, it can be a significant advantage if the device can identify the presence of CPR or motion artifacts in the ECG signal, which can obscure the true nature of the heart rhythm and thus cause the device to misdirect the user to cease administration of CPR and stand back for a defibrillating shock.

As those skilled in the art can appreciate, a common problem in prior art AEDs is identifying and eliminating these CPR and motion artifacts from the underlying ECG rhythm, which can cause the defibrillator to misinterpret the rhythm as described hereinabove.

In view of this problem, the defibrillator of the present invention uses the patient's transthoracic impedance signal, independently of the patient's ECG signal, to determine if the patient's ECG signal is distorted due to the presence of CPR or motion artifacts. In other words, the defibrillator analyzes the patient's transthoracic impedance signal to determine if CPR is being administered and/or if the patient is undergoing motion, in which case CPR and/or motion artifacts will be present in the patient's ECG signal, therefore altering the patient's base ECG signal so as to render it unreliable for diagnosis. Significantly, the present invention uses the transthoracic impedance signal independently of the ECG signal to determine if the ECG signal is distorted due to the presence of CPR and/or motion artifacts.

Figure 11:
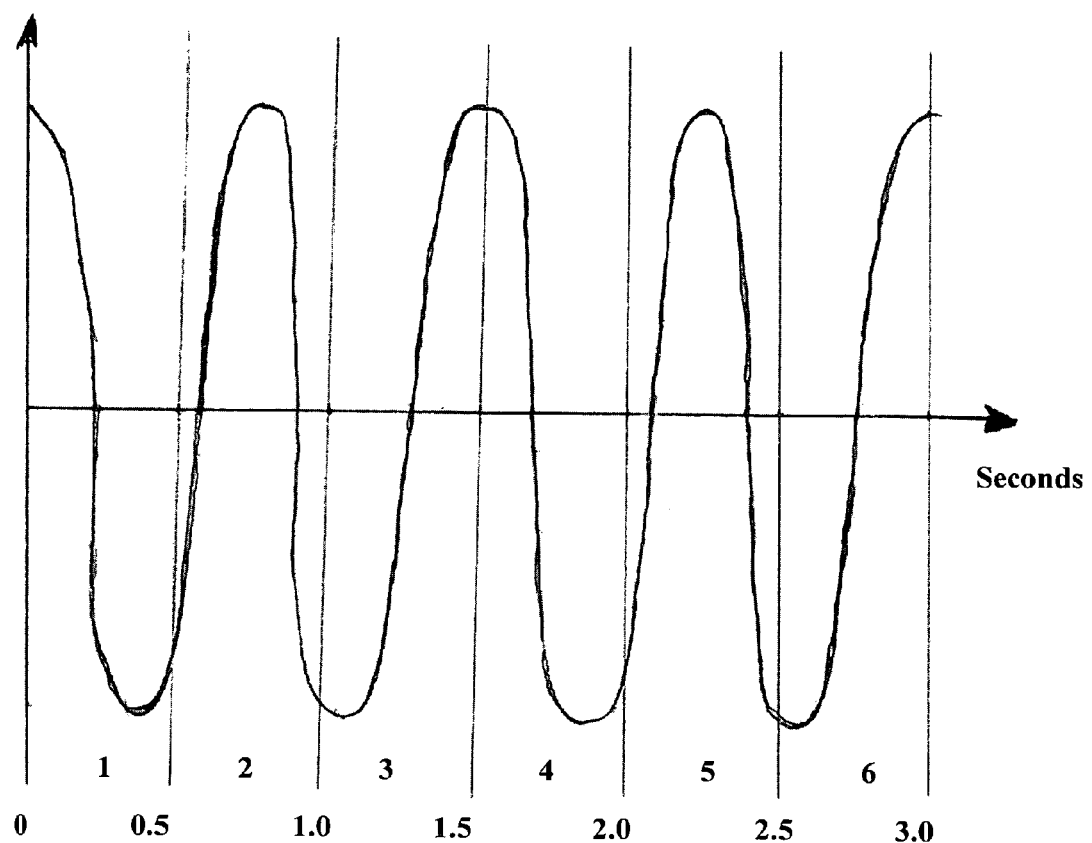
FIG. 11 is a diagram of an impedance signal over time.

The current invention achieves this by measuring variations in the impedance signal. As shown in FIG. 11, the impedance signal is sampled, the sampled impedance signal is smoothed using a signal averaging technique, and the smoothed impedance signal is stored in the device memory. The signal averaging down-samples the rate to 100 samples per second. The defibrillator uses the most current 3-second period to evaluate the impedance signal. The 3-second period is further divided into 0.5-second segments. The 0.5-second segments are classified in a binary fashion as either noisy (containing CPR and/or motion artifact) or not noisy. The defibrillator of the present invention only considers signal frequencies greater than approximately 0.66 Hz for this classification. The defibrillator determines if the 0.5-second segment is noisy by comparing impedance variation from peak-to-trough or trough-to-peak to a preset threshold. For example, the current invention uses a 10.5 ohm threshold to determine if the segment is noisy, but other thresholds may be used as well. Thus, if the impedance delta exceeds 10.5 ohms, the segment is classified as noisy. These 0.5 segments are used to create a binary sequence over the 3-seconds. The sequence is evaluated for a criterion of CPR and/or motion artifact. This may be "n-out-of-6" segments or related to a number of consecutive segments within the 3-second period. If the 3-second period is declared noisy, then the device interrupts the ECG analysis for the corresponding ECG segment and allows the rescuer to continue performing CPR. The device also notifies the rescuer that the ECG analysis has been interrupted by displaying a message on the LCD. In high motion situations, the ECG is interrupted until the device can appropriately assess the patient's rhythm.

In other words, with the defibrillator of the present invention, the device simultaneously tracks the patient's ECG signal and changes in transthoracic impedance. By way of example but not limitation, when the device detects the appearance of a VF state in the ECG signal, the device checks to see if this state accompanied by changes in the thoracic impedance signal which are indicative of the presence of CPR and/or patient motion; if so, the device notes that the measured ECG signal may not be indicative of a true VF state, and therefore does not recommend defibrillation shock. On the other hand, if the appearance of the VF state in the ECG signal is not accompanied by changes in the transthoracic impedance signal indicative of CPR and/or patient motion, the device concludes that the measured ECG signal is reflective of the true VF state and therefore recommends defibrillation shock.

It will, of course, be appreciated that, as shown in FIG. 12, it may be desirable to set different impedance thresholds at different modes of the device's function to optimize operation of the device. For example, it may be desirable to set a relatively high impedance threshold during the "analyze rhythm", "shock advised" and "press to shock" phases of the device's operation whereby to reduce the likelihood of determining that there is a CPR and/or patient motion condition during those phases; correspondingly, it may be desirable to set a relatively low impedance threshold during the "check patient" and "CPR pause" phases of the device's operation whereby to increase the likelihood of determining that there is a CPR and/or patient motion condition during those phases.

Additionally, the defibrillator of the present invention allows the rescuer to continue to perform CPR without interruption, but dependent on the operating mode, the device may periodically prompt the user to stand clear and re-analyze the patient's rhythm. For example, the defibrillator may allow the user to perform CPR uninterrupted in "check patient" mode for a time period of one minute before prompting to re-analyze the patient's rhythm.

MODIFICATIONS

It is to be understood that the present invention is by no means limited to the particular constructions herein disclosed and/or shown in the drawings, but also comprises any modifications or equivalents within the scope of the invention.

What is claimed is:

1. A method for detecting in an electrocardiogram of a patient artifact signals caused by CPR and patient motion, independently of the patient's electrocardiogram signal, the method comprising:

obtaining samples of transthoracic impedance signals of the patient independently of the patient's electrocardiogram signal by acquiring and monitoring and measuring impedance signal data from the patient for a given time period by application to the patient of a constant current input signal to produce an output voltage in proportion to the patient's impedance, and using such samples as an indicator of underlying ECG rhythm classification;

simultaneously tracking the patient's electrocardiogram signals and changes in the output voltage proportionate to the transthoracic impedance;

sensing the condition of the patient's heart by an ECG sensing current;

dividing the transthoracic impedance samples into equal three-second segments of time, each segment of time comprising impedance signal data for the segment of time, and dividing each of the three-second segments into 0.5-second samples of impedence and classifying the impedance signal data in each 0.5-second segment of time as a segment containing non-shockable artifact signals or not containing artifact signals and therefore shockable; and evaluating the three-second segments to detect the presence of CPR and for characteristics indicative of artifact signals caused by CPR and patient motion;

whereby to detect the presence of CPR and motion defects in the ECG signal and thereby improve determinations of shockable conditions.

2. A method according to claim 1 wherein classifying the impedance signal data comprises comparing the impedance signal data to a predetermined threshold.

3. A method according to claim 2 wherein the predetermined threshold comprises a 10.5 ohm threshold.

4. Apparatus for detecting in an electrocardiogram of a patient artifact signals caused by CPR and patient motion by analyzing variations in a patient's transthoracic impedance; the apparatus comprising:

electrodes for passing an impedance-sensing signal through a patient in order to obtain a sample of an impedance signal of the patient, wherein the sample comprises impedance signal data for a selected time period with no compacitive reactance from the impedance of the patient;

an impedance measuring circuit connected to said electrodes for measuring the sample of the impedance signal of the patient independently of the patient's electrocardiogram signal;

a conversion circuit for digitizing the sample of the impedance signal of the patient; and a microprocessor for (i) dividing the sample of the impedance signal into three-second segments of time, each segment of time comprising impedance signal data for a segment of the given time period; (ii) classifying said impedance signal data in each segment of time as one of (1) a segment containing artifact signals or (2) a segment not containing artifact signals; and (iii) evaluating the segments for characteristics indicative of CPR and patient motion, to determine whether the patient's electrocardiogram signal is distorted due to presence of CPR or motion artifacts.

5. Apparatus according to claim 4 wherein classifying said impedance signal data comprises comparing said impedance signal data to a predetermined threshold.

6. Apparatus according to claim 5 wherein the predetermined threshold comprises a 10.5 ohm threshold.

7. Apparatus according to claim 5 wherein the predetermined threshold is varied dependent on the operating mode of the device.

8. Apparatus according to claim 4 wherein the sample is stored in memory prior to evaluating the segments.

* * * * *